(12) United States Patent
Cullen

(10) Patent No.: US 12,311,340 B2
(45) Date of Patent: May 27, 2025

(54) CATALYST AND A PROCESS FOR THE PRODUCTION OF ETHYLENICALLY UNSATURATED CARBOXYLIC ACIDS OR ESTERS

(71) Applicant: MITSUBISHI CHEMICAL UK LIMITED, Billingham (GB)

(72) Inventor: Adam Cullen, Redcar (GB)

(73) Assignee: Mitsubishi Chemical UK Limited, Billingham (GB)

( * ) Notice: Subject to any disclaimer, the term of this patent is extended or adjusted under 35 U.S.C. 154(b) by 575 days.

(21) Appl. No.: 17/690,518

(22) Filed: Mar. 9, 2022

(65) Prior Publication Data

US 2022/0193636 A1 Jun. 23, 2022

Related U.S. Application Data

(63) Continuation of application No. 17/438,594, filed as application No. PCT/GB2020/050648 on Mar. 13, 2020, now Pat. No. 12,059,669.

(30) Foreign Application Priority Data

Mar. 13, 2019 (GB) ..................................... 1903452

(51) Int. Cl.
  *B01J 21/06* (2006.01)
  *B01J 6/00* (2006.01)
  *B01J 21/08* (2006.01)

(52) U.S. Cl.
  CPC ............. *B01J 21/063* (2013.01); *B01J 6/001* (2013.01); *B01J 21/08* (2013.01)

(58) Field of Classification Search
  CPC ....... C07C 51/09; C07C 67/343; C07C 57/04; C07C 69/54; B01J 37/0207; B01J 21/08; B01J 23/04
  See application file for complete search history.

(56) References Cited

U.S. PATENT DOCUMENTS

| | | |
|---|---|---|
| 4,218,345 A | 8/1980 | Hoff et al. |
| 4,308,172 A | 12/1981 | McDaniel |
| 4,357,451 A | 11/1982 | McDaniel |
| 5,583,085 A | 12/1996 | Ward |
| 6,544,924 B1 | 4/2003 | Jackson et al. |
| 6,887,822 B2 | 5/2005 | Hu |
| 7,247,594 B2 | 7/2007 | Jayaratne et al. |
| 10,065,976 B2 | 9/2018 | Tonks et al. |
| 2009/0163681 A1 | 6/2009 | McDaniel et al. |
| 2009/0203933 A1 | 8/2009 | Ryu |
| 2012/0232181 A1 | 9/2012 | Reiter et al. |
| 2013/0137839 A1 | 5/2013 | Yu et al. |
| 2014/0271428 A1 | 9/2014 | Gerlach et al. |
| 2015/0065667 A1 | 3/2015 | Cheng et al. |
| 2021/0213428 A1 | 7/2021 | Botha et al. |

FOREIGN PATENT DOCUMENTS

| | | | |
|---|---|---|---|
| EP | 1040869 A2 | 10/2000 | |
| JP | H115030 A | 1/1999 | |
| JP | 2000-279809 A2 | 10/2000 | |
| JP | 2005193226 A | 7/2005 | |
| RU | 2013104203 A | 8/2014 | |
| RU | 2015143278 A | 4/2017 | |
| WO | 99/52628 A1 | 10/1999 | |
| WO | 03/026795 A1 | 4/2003 | |
| WO | 2007078133 A1 | 7/2007 | |
| WO | 2009/003722 A1 | 1/2009 | |
| WO | 2012/001394 A1 | 1/2012 | |
| WO | 2012/036445 A2 | 3/2012 | |
| WO | 2014053818 A1 | 4/2014 | |
| WO | WO-2016166525 A1 * | 10/2016 | ........... C07C 51/353 |
| WO | 2018029548 A1 | 2/2018 | |
| WO | 2019099292 A1 | 5/2019 | |

OTHER PUBLICATIONS

International Search Report (ISR) for PCT/GB2020/050648 mailed Jun. 8, 2020 (4 pages).
Written Opinion for PCT/GB2020/050648 mailed Jun. 8, 2020 (7 pages).
Markus Widenmeyer et al., "TiO overlayers on MCM-48 silica by consecutive grafting", Microporous and Mesoporous Materials, vol. 44, p. 327-336, Jun. 13, 2000.
Thomas Deschner et al., "Functionalization of MCM-41 and SBA-1 with titanium(iv) (silyl)amides+", Journal of Materials Chemistry, Royal Society of Chemistry, GB, vol. 21, No. 15, p. 5620-5628, Jan. 1, 2011.
International Preliminary Report on Patentability (IPRP) for PCT/GB2020/050648 mailed Aug. 25, 2021 (8 pages).
GB Search Report for GB App. No. GB1903452.9 mailed Sep. 12, 2019 (i pages).
Olshanova K.M., Piskare'yva S.K., Barashkov K.M. "Analytic chemistry", study guide for secondary technical schools, Moscow, Chemistry, 1980, p. 42.
Chemical kinetics and catalysis. Panchenkov G.M., Lebedev V.P. Publishing house: "Chemistry", 1985.—590 pages, in particular p. 411).
English translation of May 19, 2023 Russian Office Action for RU Pat. App. 2021129631 (10 pages).

(Continued)

*Primary Examiner* — Jafar F Parsa
(74) *Attorney, Agent, or Firm* — Shumaker, Loop & Kendrick, LLP

(57) ABSTRACT

A catalyst including a modified silica support having a titanium modifier metal, and a catalytic metal on the modified silica support. A proportion of the modifier metal is present in the form of mononuclear titanium moieties or is derived from a mononuclear titanium cation source at the commencement of modification. The invention also discloses a corresponding modified silica support, a method of producing the catalyst or the modified silica support, and a process for preparing an ethylenically unsaturated acid or ester in the presence of the catalyst.

6 Claims, No Drawings

(56) References Cited

OTHER PUBLICATIONS

Hou et al., "Synthesis of a mononuclear Ti complex: A molecular precursor strategy for control of silica supported single siite Ti decorated Au catalysts for cyclooctene expoxidation", Applied Surface Science, vol. 455 pp. 561-569 (Year: 2018).
Restriction Requirement issued for U.S. Appl. No. 17/438,594, mailed Jul. 3, 2023 (9 pages).
Non-Final Office Action issued for U.S. Appl. No. 17/438,594, mailed Dec. 29, 2023 (9 pages).
Notice of Allowance (NOA) issued for U.S. Appl. No. 17/438,594, mailed May 1, 2024 (7 pages).
English Abstract Only of Kolesnikov et al., "Solid Catalysts, their structure, composition and catalytic activity: Monograph 1", M: Publishing House Oil and Gas of Russian State University of Oil and Gas named after I.M. Gubkin, 2000, 372 pp, in particular, p. 10).
Corrected Notice of Allowability issued for U.S. Appl. No. 17/438,594, mailed May 13, 2024 (3 pages).
Corrected Notice of Allowability issued for U.S. Appl. No. 17/438,594, mailed May 31, 2024 (3 pages).

\* cited by examiner

CATALYST AND A PROCESS FOR THE PRODUCTION OF ETHYLENICALLY UNSATURATED CARBOXYLIC ACIDS OR ESTERS

TECHNICAL FIELD AND BACKGROUND

The present invention relates to a modified silica catalyst support, a catalyst incorporating the modified silica support and a process for the production of ethylenically unsaturated carboxylic acids or esters, particularly α, β unsaturated carboxylic acids or esters, more particularly acrylic acids or esters such as (alk)acrylic acids or alkyl (alk)acrylates especially (meth)acrylic acids or alkyl (meth)acrylates such as methacrylic acid (MAA) and methyl methacrylate (MMA) by the condensation of carboxylic acid or esters with formaldehyde or a source thereof such as dimethoxymethane in the presence of such catalysts, in particular, by the condensation of propionic acid or alkyl esters thereof such as methyl propionate with formaldehyde or a source thereof in the presence of such catalysts. The invention is therefore particularly relevant to the production of MAA and MMA. The catalysts of the present invention incorporate a modified silica support modified by a particular modifier metal and a catalytic metal.

As mentioned above, the unsaturated acids or esters may be made by the reaction of a carboxylic acid or ester and suitable carboxylic acids or esters are alkanoic acids (or esters) of the formula $R^3$—$CH_2$—$COOR^4$, where $R^3$ and $R^4$ are each, independently, a suitable substituent known in the art of acrylic compounds such as hydrogen or an alkyl group, especially a lower alkyl group containing, for example, 1-4 carbon atoms. Thus, for instance, MAA or alkyl esters thereof, especially MMA, may be made by the catalytic reaction of propionic acid, or the corresponding alkyl ester, e.g. methyl propionate, with formaldehyde as a methylene source in accordance with the reaction sequence 1.

and

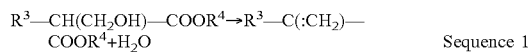

Sequence 1

An example of reaction sequence 1 is reaction sequence 2

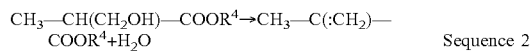

Sequence 2

The above reaction sequences are typically effected at an elevated temperature, usually in the range 250-400° C., using an acid/base catalyst. Where the desired product is an ester, the reaction is typically effected in the presence of the relevant alcohol in order to minimise the formation of the corresponding acid through hydrolysis of the ester. Also for convenience it is often desirable to introduce the formaldehyde in the form of a complex of formaldehyde with methanol. Hence, for the production of MMA, the reaction mixture fed to the catalyst will generally consist of methyl propionate (MEP), methanol, formaldehyde and water.

A known production method for MMA is the catalytic conversion of MEP to MMA using formaldehyde. A known catalyst for this is a caesium catalyst incorporating a support, for instance, silica.

SUMMARY

The present inventor has now discovered that catalysts comprising certain silica supports modified by titanium metal, and containing the catalytic metal, provide a high level of selectivity in the condensation of methylene sources such as formaldehyde with a carboxylic acid or alkyl ester such as MEP when at least a proportion of the modifier metal is incorporated or present in the support in the form of mononuclear titanium species.

U.S. Pat. No. 6,887,822 describes a method of making a silica hydrogel catalyst. A second metal can be used in addition to the catalytic metal. Second metals include zirconium, titanium, aluminium and iron. The metals are selected for the end use of the catalyst and titanium is taught to perform well as part of an oxidation catalyst. No teaching is provided on the nuclearity of the titanium. WO2014053818 describes depleted catalysts and their reimpregnation. It discusses that the depleted alkali metal catalyst may additionally include a second or further metal selected from the group consisting of zirconium, titanium, hafnium, aluminium, boron, and magnesium or mixtures thereof. Again no teaching is given on the nuclearity of any of the modifier metals.

However, the current inventor has surprisingly found that when the modified silica support comprises mononuclear titanium species rather than larger polynuclear titanium clusters, there is an improvement in catalytic metal binding to the modified support and thereafter higher selectivity and activity for the production of unsaturated carboxylic acids or esters by condensation of the corresponding acid or ester with a methylene source such as formaldehyde. The inventor has found that the modified silica supports providing these high selectivities contain monomeric modifier metal atoms after deposition/adsorption onto the surface of the silica.

Still further, the present inventor has found that when such modified silica supports are used, the rate of catalyst surface sintering has been found to be retarded and loss of surface area upon which the catalytic reaction takes place during the condensation reaction is reduced.

DETAILED DESCRIPTION

Therefore, catalysts comprising such modified silica supports and containing a catalytic metal are remarkably effective catalysts for the production of α, β ethylenically unsaturated carboxylic acids or esters by condensation of the corresponding acid or ester with a methylene source such as formaldehyde providing several advantages such as high levels of selectivity and/or reduced sintering of the catalyst surface.

Therefore, according to a first aspect of the present invention, there is provided a catalyst comprising
  a modified silica support,
  the modified silica support comprising titanium modifier metal;
  and a catalytic metal on the modified silica support,
  characterised in that at least a proportion, typically, at least 25%, of the said modifier metal is present in the form of mononuclear titanium moieties.

According to a second aspect of the present invention, there is provided a catalyst comprising
  a modified silica support,
  the modified silica support comprising titanium modifier metal;
  and a catalytic metal on the modified silica support, characterised in that at least a proportion, typically, at least 25%, of the said modifier metal is present in the form of modifier metal moieties derived from a mononuclear titanium cation source.

The mononuclear titanium contacts the silica support as a mononuclear titanium cation source such as a compound thereof in solution to effect adsorption of the said titanium onto the support to thereby form the titanium moieties. A suitable source may be a complex of titanium, more typically, a ligand complex in solution.

According to a third aspect of the present invention, there is provided a modified silica support for a catalyst comprising
a silica support and
titanium modifier metal,
characterised in that at least a proportion, typically, at least 25%, of the said modifier metal is present in the form of mononuclear titanium moieties.

According to a fourth aspect of the present invention, there is provided a modified silica support for a catalyst comprising
a silica support and
a titanium modifier metal,
characterised in that at least a proportion, typically, at least 25%, of the said modifier metal is present in the form of modifier metal moieties derived from a mononuclear titanium cation source at the commencement of the modification.

The modified silica support herein is modified by titanium. The modified silica support may be a co-gel of the titania and silica, however, typically, the titanium is an adsorbate adsorbed on the silica support surface. The adsorbate may be chemisorbed or physisorbed onto the silica support surface, typically, it is chemisorbed thereon. The titanium moieties are generally titanium oxide moieties.

The silica support whether the titanium is present as an adsorbate or as a co-gel is generally in the form of a silica gel, more typically, a xerogel or a hydrogel.

Typically, the titanium is adsorbed on the silica gel support surface. Therefore, typically, titanium is present on the modified silica gel support surface in the form of titanium oxide moieties.

Alternatively, titanium may be present in the support in the form of a co-gel. In such a case the modified silica support is a silica-titanium oxide gel.

Typically, the titanium is present in the modified silica support in an effective amount to reduce sintering and improve selectivity of the catalyst. Typically, at least 30%, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of titanium in the modified silica support is in mononuclear metal moieties, or is derived from a mononuclear titanium compound at the commencement of the modified silica formation at such levels.

For the avoidance of doubt, modifier metal moieties having a total of 1 metal atom are considered mononuclear. It will be appreciated that in a silica network the titanium moieties are associated with the silica network and therefore the term mononuclear moiety is a reference to the modifier metal and its immediately surrounding atoms and not to the silicon atoms of the network or to other titanium metal atoms associated with the network but nevertheless forming part of separate moieties.

Clusters of titanium of 2 metal atoms dispersed throughout the support such as a hydrogel support, have surprisingly been found to decrease reaction selectivity for the production of $\alpha$, $\beta$ ethylenically unsaturated carboxylic acids or esters by condensation of the corresponding acid or ester with a methylene source such as formaldehyde. Such large clusters have also surprisingly been found to increase sintering of the modified silica particles relative to mononuclear moieties thereby reducing the surface area which lowers strength and reduces the life of the catalyst before activity becomes unacceptably low. In addition, selectivity is often lower, depending on the nature of the cluster of the titanium.

Typically, the titanium modifier metal is uniformly distributed throughout the support surface.

Typically, the modified silica support is a xerogel. The gel may also be a hydrogel or an aerogel.

The gel may also be a silica-titania co-gel. The silica gel may be formed by any of the various techniques known to those skilled in the art of gel formation such as mentioned herein. In this case, the titania may also be distributed through the matrix of the silica as well as the surface thereof. However, typically, the modified silica gels are produced by a suitable adsorption reaction. Adsorption of the relevant titanium compounds to a silica gel such as a silica xerogel to form modified silica gel having the relevant mononuclear modifier metal moieties is a suitable technique.

As mentioned, methods for preparing silica gels are well known in the art and some such methods are described in The Chemistry of Silica: Solubility, Polymerisation, Colloid and Surface Properties and Biochemistry of Silica, by Ralph K Iler, 1979, John Wiley and Sons Inc., ISBN 0-471-02404-X and references therein.

In preferred embodiments, the mononuclear modified silica support is not formed by co-gelation i.e. not a silica-titania formed by co-gelation such as by mixing of sodium silicate solution with modifier metal complexes in sulphuric acid solution. In such embodiments, the titanium is typically incorporated as an adsorbate on the silica support surface.

Advantageously, when at least a proportion of the titanium modifier metal incorporated into the modified silica of the above aspects of the present invention is derived from a mononuclear modifier metal cation source at the commencement of the modified silica formation, there has been found to be improved reaction selectivity and/or reduced rate of sintering of the catalyst surface during the production of $\alpha$, $\beta$ ethylenically unsaturated carboxylic acids or esters.

Metal and metal oxide moieties in the modified silica support according to the present invention relate to titanium, not to silica.

Preferably, the level of titanium modifier metal present in the modified silica or catalyst may be up to $7.6 \times 10^{-2}$ mol/mol of silica, more preferably up to $5.9 \times 10^{-2}$ mol/mol of silica, most preferably up to $3.5 \times 10^{-2}$ mol/mol of silica. Typically, the level of such metal is between $0.067 \times 10^{-2}$ and $7.3 \times 10^{-2}$ mol/mol of silica, more preferably, between $0.13 \times 10^{-2}$ and $5.7 \times 10^{-2}$ mol/mol of silica and most preferably between $0.2 \times 10^{-2}$ and $3.5 \times 10^{-2}$ mol/mol of silica. Typically, the level of titanium modifier metal present is at least $0.1 \times 10^{-2}$ mol/mol of silica, more preferably, at least $0.15 \times 10^{-2}$ mol/mol of silica and most preferably at least $0.25 \times 10^{-2}$ mol/mol of silica.

Preferably, the level of titanium metal may be up to 5% w/w of the modified silica support, more preferably up to 4% w/w, most preferably up to 2.75% w/w. Typically, the level of titanium metal is between 0.05-5% w/w of the modified silica support, more preferably between 0.1-4% w/w and most preferably between 0.15-2.5% w/w. Typically, the level of titanium metal is at least 0.25% w/w of the modified silica support, such as 0.4% w/w, more typically, at least 0.5% w/w, most typically, at least 0.75% w/w.

The silica component of the modified silica support may typically form 90-99.9 wt % of the modified support, more typically 92-99.8 wt %, most typically 95-99.7 wt % thereof.

Preferably, the catalytic metal may be selected from one or more alkali metals. The catalytic metal herein is a metal other than titanium. Suitable alkali metals may be selected from potassium, rubidium and caesium, more suitably rubidium and caesium. Caesium is the most preferred catalytic metal herein.

Suitably the catalytic metals such as caesium may be present in the catalyst at a level of at least 1 mol/100 (silicon+titanium) mol more preferably, at least 1.5 mol/100 (silicon+titanium) mol, most preferably, at least 2 mol/100 (silicon+titanium) mol. The level of catalytic metal may be up to 10 mol/100 (silicon+titanium) mol in the catalyst, more preferably, up to 7.5 mol/100 (silicon+titanium) mol, most preferably, up to 5 mol/100 (silicon+titanium) mol in the catalyst.

Preferably, the level of catalytic metal in the catalyst is in the range from 1-10 mol/100 (silicon+titanium) mol, more preferably, 2-8 mol/100 (silicon+titanium) mol, most preferably, 2.5-6 mol/100 (silicon+titanium) mol in the catalyst.

Unless indicated to the contrary, amounts of modifier or catalytic metal or modifier or catalytic metal in the catalyst relate to the modifier or catalytic metal ion and not the salt.

Alternatively, the catalyst may have a wt % of catalytic metal in the range 1 to 22 wt % in the catalyst, more preferably 4 to 18 wt %, most preferably, 5-13 wt %. These amounts would apply to all alkali metals, but especially caesium.

The catalyst may comprise any suitable weight ratio of catalytic alkali metal:titanium metal. However, typically, the weight ratios for caesium:titanium are in the range from 4:1 to 20:1, more preferably from 5:1 to 18:1, most preferably from 6:1 to 15:1 in the catalyst, for rubidium:titanium are in the range from 2.5:1 to 15:1, more preferably from 3:1 to 12:1, most preferably from 4:1 to 10:1 in the catalyst. Accordingly, the catalytic metal:modifier metal mole ratio in the catalyst is typically at least 1.4 or 1.5:1, preferably, it is in the range 1.4 to 5.0:1 such as 1.5 to 4.0:1, especially, 1.5 to 3.6:1, typically in this regard the modifier metal is titanium and the catalytic metal is caesium. Generally, herein, the catalytic metal is in excess of that which would be required to neutralise the modifier metal.

Preferably, the catalytic metal is present in the range 0.5-7.0 mol/mol titanium, more preferably 1.0-6.0 mol/mol, most preferably 1.5-5.0 mol/mol titanium.

Suitably, the catalytic metal may be incorporated into the modified silica support by any method known in the art such as impregnation, co-gelation or vapour deposition with the catalytic metal.

By the term "impregnated" as used herein is included the addition of the catalytic metal dissolved in a solvent, to make a solution, which is added to the xerogel or aerogel, such that the solution is taken up into the voidages within the said xerogel or aerogel.

Typically, the catalyst of the invention may be in any suitable form. Typical embodiments are in the form of discrete particles. Typically, in use, the catalyst is in the form of a fixed bed of catalyst. Alternatively, the catalyst may be in the form of a fluidised bed of catalyst. A further alternative is a monolith reactor.

Where the catalysts are used in the form of a fixed bed, it is desirable that the supported catalyst is formed into granules, aggregates or shaped units, e.g. spheres, cylinders, rings, saddles, stars, poly-lobes prepared by pelleting, or extrusion, typically having maximum and minimum dimensions in the range 1 to 10 mm, more preferably, with a mean dimension of greater than 2 mm such as greater than 2.5 or 3 mm. The catalysts are also effective in other forms, e.g. powders or small beads of the same dimensions as indicated. Where the catalysts are used in the form of a fluidised bed it is desirable that the catalyst particles have a maximum and minimum dimension in the range of 10-500 µm, preferably 20-200 µm, most preferably 20-100 µm.

Levels of catalytic metal in the catalyst whether moles, wt % or otherwise may be determined by appropriate sampling and taking an average of such samples. Typically, 5-10 samples of a particular catalyst batch would be taken and alkali metal levels determined and averaged, for example by XRF, atomic absorption spectroscopy, neutron activation analysis, ion coupled plasma mass spectrometry (ICPMS) analysis or ion coupled plasma atomic emission spectroscope (ICPAES).

Levels of the metal oxide of particular types in the catalyst/support are determined by XRF, atomic absorption spectroscopy, neutron activation analysis or ion coupled plasma mass spectrometry (ICPMS) analysis.

The typical average surface area of the modified silica supported catalyst according to any aspect of the invention is in the range 20-600 $m^2/g$, more preferably 30-450 $m^2/g$ and most preferably 35-350 $m^2/g$ as measured by the B.E.T. multipoint method using a Micromeritics Tristar 3000 Surface Area and porosity analyser. The reference material used for checking the instrument performance may be a carbon black powder supplied by Micromeritics with a surface area of 30.6 $m^2/g$ (+/−0.75 $m^2/g$), part number 004-16833-00.)

If the catalyst material is porous, it typically extends over the mesoporous and macroporous range with an average pore size of between 2 and 1000 nm, more preferably between 3 and 500 nm, most preferably between 5 and 250 nm. Macropore size (above 50 nm) can be determined by mercury intrusion porosimetry using NIST standards whilst the Barrett-Joyner-Halenda (BJH) analysis method using liquid nitrogen at 77 K is used to determine the pore size of mesopores (2-50 nm). The average pore size is the pore volume weighted average of the pore volume vs. pore size distribution.

The average pore volume of the catalyst particles may be less than 0.1 $cm^3/g$ but is generally in the range 0.1-5 $cm^3/g$ as measured by uptake of a fluid such as water. However, microporous catalysts with very low porosity are not the most preferred because they may inhibit movement of reagents through the catalyst and a more preferred average pore volume is between 0.2-2.0 $cm^3/g$. The pore volume can alternatively be measured by a combination of nitrogen adsorption at 77 K and mercury porosimetry. The Micromeritics TriStar Surface Area and Porosity Analyser is used to determine pore volume as in the case of surface area measurements and the same standards are employed.

In the present invention, it has been found that controlling the size of the mononuclear titanium moieties is surprisingly advantageous. However, to obtain the greatest benefit it is necessary to control the proximity of neighbouring modifier metal moieties because the modifier metal moieties may otherwise combine with each other and thus increase the nuclearity of the modifier metal moiety.

Therefore, according to a fifth aspect of the present invention there is provided a method of producing a modified silica support comprising the steps of:

providing a silica support having silanol groups;

contacting the silica support with a mononuclear titanium species so that modifier metal is adsorbed onto the surface of the silica support through reaction with said silanol groups.

Preferably, the adsorbed modifier metal cations are sufficiently spaced apart from each other to substantially prevent oligomerisation thereof, more preferably di,tri or oligomerisation thereof with neighbouring modifier metal cations.

Typically, at least 25%, more typically, at least 30%, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of the said titanium species contacting the silica support in the contacting step are mononuclear species.

According to a further aspect of the present invention there is provided a method of producing a modified silica support according to any of the aspects herein or otherwise comprising the steps of:

providing a silica support having silanol groups;

treating the silica support with mononuclear titanium compounds so that titanium is adsorbed onto the surface of the silica support through reaction with silanol groups, wherein the adsorbed titanium atoms are sufficiently spaced apart from each other to substantially prevent oligomerisation thereof with neighbouring titanium atoms, more preferably, sufficiently spaced apart from each other to substantially prevent dimerisation or trimerisation thereof with neighbouring modifier metal atoms thereof.

Preferably, the spacing apart of the titanium atoms is effected by a) decreasing the concentration of silanol groups on the silica support and/or b) attaching a non-labile ligand of sufficient size to the titanium prior to treating the silica support.

According to a still further aspect there is provided a method of producing a catalyst comprising the steps of:— i. providing a silica support with isolated silanol groups and optionally treating the said support to provide isolated silanol groups (—SiOH) at a level of <2.5 groups per $nm^2$;

ii. contacting the optionally treated silica support with a mononuclear titanium modifier metal compound to effect adsorption of the said titanium onto the support, typically to at least 25% of the said isolated silanol groups;

iii. optionally, removing any solvent or liquid carrier for the titanium compounds;

iv. calcining the modified silica for a time and temperature sufficient to convert the mononuclear titanium compound adsorbed on the surface to an oxide or hydroxide of titanium;

v. treating the said calcined modified silica with a catalytic alkali metal to impregnate the modified silica with the catalytic metal to form the catalyst and optionally, calcining the catalyst.

According to an even further aspect of the present invention there is provided a method of producing a modified silica support for a catalyst comprising the steps of:— i. providing a silica support with isolated silanol groups and optionally treating the said support to provide isolated silanol groups (—SiOH) at a level of <2.5 groups per $nm^2$;

ii. contacting the optionally treated silica support with a mononuclear titanium compound to effect adsorption of the said titanium onto the support, typically to at least 25% of the said isolated silanol groups;

iii. optionally, removing any solvent or liquid carrier for the modifier metal compounds;

iv. optionally calcining the modified support for a time and temperature sufficient to convert the mononuclear titanium compound adsorbed on the surface to an oxide or hydroxide of titanium in preparation for catalyst impregnation.

Preferably, the silanol group concentration is decreased prior to treatment with the titanium compounds by calcination treatment, chemical dehydration or other suitable methods.

Preferably, the mononuclear titanium cation source herein is a solution of compounds of the said titanium so that the compounds are in solution when contacted with the support to effect adsorption onto the support.

Typically, the solvent for the said solution is other than water.

Typically, the solvent is an organic solvent such as toluene or heptane, Further, the solvent may be an aliphatic or aromatic solvent. Still further, the solvent may be a chlorinated solvent such as dichloromethane. More typically, the solvent is an aliphatic alcohol, typically selected from C1-C6 alkanols such as methanol, ethanol, propanol, isopropanol, butanols, pentanols and hexanols, more typically, methanol, ethanol or propanols.

Advantageously, the proximity of the adsorbed titanium modifier metal to neighbouring titanium modifier metal cations may be controlled by the concentration of the said titanium modifier metal in the contacting step and:— a) the concentration of silanol groups on the silica support and/or b) the size of any non-labile ligand attached to the titanium modifier metal cation.

The silanol group concentration on the silica support prior to adsorption is preferably controlled by calcination or other suitable methods as known to those skilled in the art. Methods of identification of silanols include for example L T Zhuravlev, in "Colloids and Surfaces: Physicochemical and Engineering Aspects, vol. 173, pp. 1-38, 2000" which describes four different forms of silanols: isolated silanols, geminal silanols, vicinal silanols, and internal silanols which can coexist on silica surfaces. Isolated silanol groups are most preferred. These can be identified by infrared spectroscopy as a narrow absorption peak at 3730-3750 $cm^{-1}$ whereas other silanols display broad peaks between 3460 and 3715 $cm^{-1}$ (see "The Surface Properties of Silicas, Edited by Andre P Legrand, John Wiley and Sons, 1998 (ISBN 0-471-95332-6) pp. 147-234).

By non-labile ligand is meant a ligand that is co-ordinated to the titanium modifier metal and is not removed by the adsorption of the titanium onto the silica surface. Accordingly, the non-labile ligand is typically coordinated to the titanium modifier metal in solution prior to treatment of the silica surface with titanium. For the avoidance of doubt, the non-labile ligand is typically removed by suitable treatment of the silica surface following adsorption of the titanium.

The size of the non-labile ligand is effective to space the titanium moieties apart to prevent combination thereof.

According to further aspects of the present invention there is provided methods of producing modified silica supports for a catalyst or catalysts according to the claims.

The invention extends to a modified silica support according to any of the aspects herein, wherein the support comprises isolated silanol groups (—SiOH) at a level of <2.5 groups per $nm^2$. Typically, the support comprises isolated silanol groups (—SiOH) at a level of >0.1 and <2.5 groups per $nm^2$, more preferably, at a level of from 0.2 to 2.2, most preferably, at a level of from 0.4 to 2.0 groups per $nm^2$.

Still further the invention extends to a catalyst or modified silica support according to any aspects herein, wherein the support comprises the said titanium modifier metal moieties present on the support and present at a level of <2.5 moieties per $nm^2$.

Typically, the support comprises the said titanium modifier metal moieties at a level of >0.025 and <2.5 moieties per $nm^2$, more preferably, at a level of from 0.05 to 2.0 moieties per $nm^2$, most preferably, at a level of from 0.1 to 1.5 moieties per $nm^2$.

Suitable ligands herein may be non-labile ligands optionally selected from molecules with lone pair containing oxygen or nitrogen atoms able to form 5 or 6 membered rings with a titanium atom. Examples include diones, diimines, diamines, diols, dicarboxylic acids or derivatives thereof such as esters, or molecules having two different such functional groups and in either case with the respective N or O and N or O atom separated by 2 or 3 atoms to thereby form the 5 or 6 membered ring. Examples include pentane-2,4-dione, esters of 3-oxobutanoic acid with aliphatic alcohols containing 1-4 carbon atoms such as ethyl 3-oxobutanoate, propyl 3-oxobutanoate, isopropyl 3-oxobutanoate, n-butyl 3-oxobutanoate, t-butyl 3-oxobutanoate, heptane-3,5-dione, 2,2,6,6-Tetramethyl-3,5-heptanedione, 1,2-ethanediol, 1,2-propanediol, 1,3-propanediol, 1,3-butanediol, 1,2-butanediol, 1,2-diaminoethane, ethanolamine, 1,2-diamino-1,1,2,2-tetracarboxylate, 2,3-dihydroxy-1,4-butanedioate, 2,4-dihydroxy-1,5-pentanedioate, salts of 1,2-dihydroxylbenzene-3-5-disulphonate, diethylenetriaminepentaacetic acid, nitrolotriacetic acid, N-hydroxyethylethylenediaminetriacetic acid, N-hydroxyethyliminodiacetic acid, N,N-dihydroxyethylglycine, oxalic acid and its salts. Pentane-2,4-dione, heptane-3,5-dione, 2,2,6,6-Tetramethyl-3,5-heptanedione, ethyl 3-oxobutanoate and t-butyl 3-oxobutanoate are most preferred. The smaller bidentate ligands having, for example less than 10 carbon and/or hetero atoms in total enable small complexes to be formed which can allow higher concentrations to be deposited on the surface of the silica compared to larger ligands. Accordingly, the mononuclear modifier metal cation source herein may be in the form of complexes of titanium with such smaller ligands, preferably, with at least one such ligand. Such compounds may include labile ligands such as solvent ligands, for example in alcohol solvent, alkoxide ligands such as ethoxide or propoxide etc.

The concentration of preferably isolated silanol groups determines the maximum number of sites for titanium modifier metal adsorption. By controlling this concentration, the proximity of the adsorbed titanium modifier metal can be effectively determined because the distribution of silanol sites will generally be uniform. The isolated silanol concentration for the production of a modified silica support according to the present inventions may be below 2.5 groups per $nm^2$, more typically, less than 2.0 groups per $nm^2$, most typically, less than 1.75 groups per $nm^2$. Suitable ranges for the silanol concentration for production of a modified silica supports may be 0.4-2.5 silanol groups per $nm^2$, more preferably 0.5-2.0 silanol groups per $nm^2$, most preferably 0.8-1.5 silanol groups per $nm^2$.

The concentration of the titanium modifier metal, generally in the form of a cation should be set at a level that prevents the significant formation of bilayers etc. on the surface of the support which would lead to titanium metal to metal interaction. In addition, filling in of gaps in the initial monolayer that could result in weak adsorption of the titanium modifier metal away from silanol sites should also be avoided to prevent interaction with neighbouring strongly adsorbed titanium modifier metals. Typical concentration ranges for the titanium modifier metals of the invention may be as set out herein.

Typically, at least 30%, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of the titanium modifier metal in the modifier metal compounds are mononuclear modifier metal compounds when the source thereof is contacted with the support to effect adsorption of the said compounds onto the support.

According to a further aspect of the present invention there is provided a method of producing a catalyst comprising
  a modified silica support,
  the modified silica support comprising a titanium modifier metal;
  and a catalytic metal on the modified silica support,
  characterised in that at least a proportion, typically, at least 25%, of the said modifier metal is present in the form of mononuclear titanium moieties
  the said method comprising
  the steps of:—
  treating the silica support to provide isolated silanol groups (—SiOH) at a level <2.5 groups per $nm^2$;
  reacting the treated support with mononuclear titanium compounds to effect bonding thereof to at least 25% of the said isolated silanol groups;
  optionally, removing any solvent or liquid carrier;
  calcining the modified silica for a time and temperature sufficient to convert the mononuclear titanium compound adsorbed on the surface to an oxide or hydroxide of titanium;
  treating the said calcined modified silica with a catalytic alkali metal to impregnate the modified silica with the catalytic metal.

Advantageously, by providing a smaller number of isolated silanol sites and by bonding mononuclear titanium species to these sites a catalyst support is provided that leads to improved selectivity of the catalyst, lower sintering rate and better ageing of catalyst.

A suitable method of treating the silica to provide the isolated silanol groups at the level specified is by calcination. However, other techniques such as hydrothermal treatment or chemical dehydration are also possible. U.S. Pat. No. 5,583,085 teaches chemical dehydration of silica with dimethyl carbonate or ethylene dicarbonate in the presence of an amine base. U.S. Pat. Nos. 4,357,451 and 4,308,172 teach chemical dehydration by chlorination with $SOCl_2$ followed by dechlorination with $H_2$ or ROH followed by oxygen in a dry atmosphere. Chemical dehydration may provide up to 100% removal of silanols against a minimum of 0.7/nm² by thermal treatment. Thus, in some instances, chemical dehydration may provide more scope for silanol group control.

The term isolated silanol (also known as single silanol) is well known in the art and distinguishes the groups from vicinal or geminal or internal silanols. Suitable methods for determining the incidence of isolated silanols include surface sensitive infrared spectroscopy and $^1$H NMR or $^{31}$Si NMR.

According to a sixth aspect of the present invention there is provided a method of producing a catalyst according to any previous aspects of the present invention, comprising the steps of: forming a modified silica according to any previous aspect, and contacting the modified silica support with a solution containing a catalytic metal to impregnate the modified silica with the catalytic metal.

Preferably, the silica support is dried or calcined prior to treatment with the titanium cation source. The modified silica formed may irrespective of whether previously dried or calcined be dried or calcined prior to addition of the catalytic metal.

The silica may be in the form of a gel prior to treatment with the modifier metal. The gel may be in the form of a hydrogel, a xerogel or an aerogel at the commencement of modification.

The silica support may be a xerogel, hydrogel or aerogel. Preferably, the silica support is a xerogel.

The silica support may be treated by the mononuclear modifier metal cation source by any of the various techniques known to those skilled in the art of support formation. The silica support may be contacted with the mononuclear modifier metal cation source in such a manner so as to disperse modifier metal throughout the silica support. Typically, the titanium may be uniformly distributed throughout the surface of the silica support. Preferably, titanium modifier metal is dispersed through the silica support by adsorption.

By the term "adsorption" or the like in relation to the titanium modifier metal as used herein is meant the incorporation of modifier metal onto the silica support surface by the interaction of the titanium cation source with the silica support, typically by chemisorption. Typically, addition of the modifier to the silica support involves the steps of: adsorption of the metal cation source onto the silica support to form an organic metal complex and calcination of the complex to convert the organic metal complexes to metal oxide moieties. Typically, there is therefore a uniform distribution of modifier metal throughout the silica support. Typically, titanium is dispersed throughout the silica support.

Examples of suitable metal cation sources herein include organic complexes such as titanium tetrakis(methoxide), titanium tetrakis(ethoxide), titanium tetrakis(n-propoxide), titanium tetrakis(i-propoxide), titanium tetrakis(n-butoxide), titanium tetrakis(t-butoxide), titanium tetrakis(2-ethylhexyloxide), titanium oxide bis(acetylacetonate), titanium oxide bis(2,2,6,6-tetramethyl-3,5-heptanedionate), titanium (triethanolaminato)isopropoxide, titanium bis(triethanolamine) di-isopropoxide, titanium tetrakis(diethylamide), titanium tetrakis(ethylmethylamide), titanium tetrakis(dimethylamide), titanium tetrakis(neopentyl), titanium(IV) bis(ammonium lactate)dihydroxide and metal salts such as titanium (IV) oxysulphate, titanium(IV) oxynitrate, titanium(IV) oxychloride. Typically, the mononuclear modifier metal cation source is provided as an organic complex.

Typically, the titanium modifier metal is contacted with the silica support in solution Preferably, the titanium modifier metal cation source is provided in any solvent in which the metal cation source is soluble. Examples of suitable solvent include water or alcohols. Preferred solvents are alcohols such as methanol, ethanol, propanol, isopropanol, butanols, pentanols and hexanols.

Preferably, the titanium modifier metal cation source is added to the silica as a metal salt in such alcoholic solution.

In one embodiment, the metal cation source is provided as a solution of one or more of titanium tetrakis(methoxide), titanium tetrakis(ethoxide), titanium tetrakis(n-propoxide), titanium tetrakis(i-propoxide), titanium tetrakis(n-butoxide) titanium tetrakis(t-butoxide), titanium tetrakis(2-ethylhexyloxide), titanium oxide bis(acetylacetonate), titanium oxide bis(2,2,6,6-tetramethyl-3,5-heptanedionate), titanium (triethanolaminato)isopropoxide, titanium bis(triethanolamine) di-isopropoxide, titanium tetrakis(diethylamide), titanium tetrakis(ethylmethylamide), titanium tetrakis(dimethylamide), titanium tetrakis(neopentyl) titanium(IV) bis(ammonium lactate)dihydroxide in one of methanol, ethanol, isopropanol, propanol, butanol, isobutanol, or 2-butanol, optionally, with up to 20% water by volume.

Preferably, after adsorption of the modifier metal onto the silica support, the solvent is removed by evaporation.

Optionally, the modified silica support is calcined to remove any ligands or other organics from the modified support.

It will be understood by a skilled person that the catalytic metal may be added to the modified silica by any suitable means. Typically, in order to produce the modified silica catalyst, the modified silica is contacted with a catalytic metal.

Typically, in order to produce the catalyst, the modified silica support is contacted with an acidic, neutral or alkaline aqueous solution containing a catalytic metal such as caesium, in the form of a salt of a catalytic metal and a base. Alternatively, the support can be contacted with a water miscible solution of the catalytic metal salt in an organic solvent. Preferred solvents are alcohols such as methanol, ethanol, propanol and isopropanol, preferably methanol. The most preferred solvent is methanol. Most preferably, the catalytic metal is added as a salt solution in methanol. Low levels of water, typically up to 20 vol % can be contained in the solutions.

Typically, the conditions of temperature, contact time and pH during this stage of the catalyst production process are such as to allow for impregnation of the modified silica support with the catalytic metal to form a modified silica supported catalyst.

Typical conditions of temperature for this step are between 5-95° C., more typically 10-80° C. and most typically between 20-70° C. The temperature for this step may be at least 5° C., more typically at least 10° C., most typically, at least 20° C.

Typical contact times between the modified support and the catalytic metal containing solution for this step may be between 0.05-48 hours, more typically between 0.1-24 hours, most typically between 0.5-18 hours. The contact time may be at least 0.05 hours, more typically at least 0.1 hours, most typically at least 0.5 hours.

The concentration of the catalytic metal salt solution for this step is dependent on a large number of factors including the solubility limit of the catalytic metal compound, the porosity of the modified silica support, the desired loading of the catalytic metal on the support and the method of addition, including the amount of liquid used to impregnate the support, the pH and the choice of the catalytic metal compound. The concentration in solution is best determined by experiment.

Suitable salts of catalytic metals for incorporation of the catalytic metal generally may be selected from one or more of the group consisting of formate, acetate, propionate, hydrogen carbonate, chloride, nitrate, hydroxide and carbonate, more typically, hydroxide, acetate or carbonate and most typically hydroxide and/or carbonate. The pH can be controlled during the impregnation by addition of ammonia with the metal compound or by using an appropriate catalytic metal compound such as the formate, carbonate, acetate or hydroxide, more preferably, the hydroxide or carbonate, in all cases either alone, in combination, or together with an appropriate carboxylic acid. The control of the pH in the preferred ranges is most important at the end of the impregnation to effect satisfactory adsorption. Most typically, these salts may be incorporated using an alkaline solution of the salt. If the salt is not itself alkaline then a suitable base such as ammonium hydroxide may be added. As hydroxide salts are basic in nature, mixtures of one or more of the above salts with the hydroxide salt of the particular catalytic metal such as caesium may conveniently be prepared.

It will be understood by the skilled person that a catalytic metal of the present invention may be added to the modified silica support by any suitable means. The catalyst may be fixed, typically by calcination, onto the support after deposition of the compound onto the support optionally using a suitable aqueous salt and subsequent drying of the surface coated support.

Generally, drying of the modified silica support is achieved by appropriate methods known to the skilled person such as in a drying unit or oven.

Typically, the catalyst contains between 0.01-25% w/w water, more typically 0.1-15% w/w water and most typically between 0.5%-5.0 w/w water.

Optionally, the modified silica supported catalyst containing catalytic metal may be dried or calcined, the process of calcination is well known to those skilled in the art.

In some cases, it may be necessary to calcine the support formed from the modification stage at 200-1000° C., more typically, 300-800° C., most typically, 350-600° C. prior to addition of the catalytic metal. In preferred calcinations of the support formed from the modification stage, the temperature is at least 375° ° C., such as 400° C. or 450° C. The calcination atmosphere should typically contain some oxygen, suitably 1-30% oxygen and most suitably 2-20% oxygen to effect removal of the organic residues as carbon dioxide and water. The calcination time may typically be between 0.01 and 100 hours, suitably 0.5-40 hours, most suitably 1-24 hours. The calcined support such as xerogel material should be cooled to the appropriate temperature for impregnation. Addition of the catalytically active metal can be carried out by methods described for the uncalcined material or can be by any other normal method used to impregnate catalyst supports, such as xerogel supports, such as using a solvent other than water such as an alcohol, suitably methanol, ethanol, propanol or isopropanol or using the incipient wetness method where only sufficient solution is added to the xerogel supports to fill the pores of the xerogel support. In this case, the concentration of the catalytically active metal may be calculated so as to introduce the target amount of catalytically active metal to the xerogel support material rather than providing an excess of solution of lower concentration by the method described earlier. The addition of the catalytically active metal may utilise any preferred methodology known in the art. The calcining technique is particularly advantageous where an organic complex is used as the source of the titanium as it may be necessary to modify the subsequent catalyst preparation procedure so as to remove at least a fraction of the organic complexing salt prior to impregnation with caesium. Advantageously, it has been found that the catalytic metal:modifier metal ratio and therefore the catalytic metal required is lowered by the calcination of the modified support. This was unexpected and provides a further improvement to the invention.

According to a seventh aspect of the present invention there is provided a method of producing an ethylenically unsaturated carboxylic acid or ester, typically, an α, β ethylenically unsaturated carboxylic acid or ester, comprising the steps of contacting formaldehyde or a suitable source thereof with a carboxylic acid or ester in the presence of catalyst and optionally in the presence of an alcohol, wherein the catalyst is according to any of the other aspects of the present invention defined herein.

Advantageously, it has also been found that catalysts comprising modified silicas as defined herein and containing a catalytic metal are remarkably effective catalysts for the production of α, β ethylenically unsaturated carboxylic acid or esters by condensation of the corresponding acid or ester with a methylene source such as formaldehyde having reduced sintering of the catalyst surface, improved selectivity and providing high catalyst surface area. In particular enhanced properties are found when using mononuclear titanium moieties and/or when the modified silica support is calcined prior to treatment with the catalytic metal. Furthermore, the use of certain metal complexes to incorporate the titanium modifier metal onto the support by adsorption provides a convenient source of mononuclear titanium moieties. Such a source also allows control of the nature of the titanium modifier metal and provides a more uniform distribution of mononuclear titanium moieties.

By the term "a suitable source thereof" in relation to formaldehyde herein is meant that the free formaldehyde may either form in situ from the source under reaction conditions or that the source may act as the equivalent of free formaldehyde under reaction conditions, for example it may form the same reactive intermediate as formaldehyde so that the equivalent reaction takes place.

A suitable source of formaldehyde may be a compound of formula (I):

(I)

wherein $R^5$ and $R^6$ are independently selected from $C_1$-$C_{12}$ hydrocarbons or H, X is O, n is an integer from 1 to 100, and m is 1.

Typically, $R^5$ and $R^6$ are independently selected from $C_1$-$C_{12}$ alkyl, alkenyl or aryl as defined herein, or H, more suitably, $C_1$-$C_{10}$ alkyl, or H, most suitably, $C_1$-$C_6$ alkyl or H, especially, methyl or H. Typically, n is an integer from 1 to 10, more suitably 1 to 5, especially, 1-3.

However, other sources of formaldehyde may be used including trioxane.

Therefore, a suitable source of formaldehyde also includes any equilibrium composition which may provide a source of formaldehyde. Examples of such include but are not restricted to dimethoxymethane, trioxane, polyoxymethylenes $R^1$—O—$(CH_2$—O$)_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate.

Polyoxymethylenes are higher formals or hemiformals of formaldehyde and methanol $CH_3$—O—$(CH_2$—O$)_i$—$CH_3$ ("formal-i") or $CH_3$—O—$(CH_2$—O$)_i$—H ("hemiformal-i"), wherein i=1 to 100, suitably, 1-5, especially 1-3, or other polyoxymethylenes with at least one non methyl terminal group. Therefore, the source of formaldehyde may also be a polyoxymethylene of formula $R^{31}$—O—(CH2-O—), $R^{32}$, where $R^{31}$ and $R^{32}$ may be the same or different groups and at least one is selected from a $C_1$-$C_{10}$ alkyl group, for instance $R^{31}$=isobutyl and $R^{32}$=methyl.

Generally, the suitable source of formaldehyde is selected from dimethoxymethane, lower hemiformals of formaldehyde and methanol, $CH_3$—O—$(CH_2$—O$)_i$—H where i=1-3, formalin or a mixture comprising formaldehyde, methanol and methyl propionate.

Typically, by the term formalin is meant a mixture of formaldehyde:methanol:water in the ratio 25 to 65%:0.01 to 25%:25 to 70% by weight. More typically, by the term formalin is meant a mixture of formaldehyde:methanol:water in the ratio 30 to 60%:0.03 to 20%:35 to 60% by weight. Most typically, by the term formalin is meant a mixture of formaldehyde:methanol:water in the ratio 35 to 55%:0.05 to 18%:42 to 53% by weight.

Typically, the mixture comprising formaldehyde, methanol and methyl propionate contains less than 5% water by weight. More suitably, the mixture comprising formaldehyde, methanol and methyl propionate contains less than 1% water by weight. Most suitably, the mixture comprising formaldehyde, methanol and methyl propionate contains 0.1 to 0.5% water by weight.

According to an eighth aspect of the present invention, there is provided a process for preparing an ethylenically unsaturated acid or ester comprising contacting an alkanoic acid or ester of the formula $R^1$—$CH_2$—$COOR^3$, with formaldehyde or a suitable source of formaldehyde of formula (I) as defined below:

(I)

where R5 is methyl and R6 is H;
X is O;
m is 1;
and n is any value between 1 and 20 or any mixture of these;
in the presence of a catalyst according to any aspect of the present invention, and optionally in the presence of an alkanol; wherein R1 is hydrogen or an alkyl group with 1 to 12, more Suitably, 1 to 8, most suitably, 1 to 4 carbon atoms and R3 may also be independently, hydrogen or an alkyl group with 1 to 12, more suitably, 1 to 8, most suitably, 1 to 4 carbon atoms.

Therefore, the present inventor has discovered that having titanium in the form of mononuclear oxide moieties according to the present invention enables surprising improvement in selectivity for the condensation of methylene sources such as formaldehyde with a carboxylic acid or alkyl ester such as methyl propionate to form ethylenically unsaturated carboxylic acids. In addition, the rate of sintering of the catalyst surface during the condensation reaction is significantly and surprisingly reduced.

Accordingly, one particular process for which the catalysts of the present invention have been found to be particularly advantageous is the condensation of formaldehyde with methyl propionate in the presence of methanol to produce MMA.

In the case of production of MMA, the catalyst is typically contacted with a mixture comprising formaldehyde, methanol and methyl propionate.

The process of the seventh or eighth aspect of the invention is particularly suitable for the production of acrylic and alkacrylic acids and their alkyl esters, and also methylene substituted lactones. Suitable methylene substituted lactones include 2-methylene valerolactone and 2-methylene butyrolactone from valerolactone and butyrolactone respectively. Suitable, (alk)acrylic acids and their esters are $(C_{0-8}alk)$ acrylic acid or alkyl $(C_{0-8}alk)$acrylates, typically from the reaction of the corresponding alkanoic acid or ester thereof with a methylene source such as formaldehyde in the presence of the catalyst, suitably the production of methacrylic acid, acrylic acid, methyl methacrylate, ethyl acrylate or butyl acrylate, more suitably, methacrylic acid or especially methyl methacrylate (MMA) from propanoic acid or methyl propionate respectively. Accordingly, in the production of methyl methacrylate or methacrylic acid, the preferred ester or acid of formula $R^1$—$CH_2$—$COOR^3$ is methyl propionate or propionic acid respectively and the preferred alkanol is therefore methanol. However, it will be appreciated that in the production of other ethylenically unsaturated acids or esters, the preferred alkanols or acids will be different.

The reaction of the present invention may be a batch, semi-batch or continuous reaction. Typical conditions of temperature and gauge pressure in the process of the seventh or eighth aspect of the invention are between 100° C. and 400° C., more preferably, 200° C. and 375° C., most preferably, 275° C. and 360° C.; and/or between 0.001 MPa and 1 MPa, more preferably between 0.03 MPa and 0.5 MPa, most preferably between 0.03 MPa and 0.3 MPa. Typical residence times for the reactants in the presence of the catalyst are between 0.1 and 300 secs, more preferably between, 1-100 secs, most preferably between 2-50 secs, especially, 3-30 secs.

The amount of catalyst used in the process of production of product in the present invention is not necessarily critical and will be determined by the practicalities of the process in which it is employed. However, the amount of catalyst will generally be chosen to effect the optimum selectivity and yield of product and an acceptable temperature of operation. Nevertheless, the skilled person will appreciate that the minimum amount of catalyst should be sufficient to bring about effective catalyst surface contact of the reactants. In addition, the skilled person would appreciate that there would not really be an upper limit to the amount of catalyst relative to the reactants but that in practice this may be governed again by the contact time required and/or economic considerations.

The relative amount of reagents in the process of the seventh or eighth aspect of the invention can vary within wide limits but generally the mole ratio of formaldehyde or suitable source thereof to the carboxylic acid or ester is within the range of 20:1 to 1:20, more suitably, 5:1 to 1:15. The most preferred ratio will depend on the form of the formaldehyde and the ability of the catalyst to liberate formaldehyde from the formaldehydic species. Thus highly reactive formaldehydic substances where one or both of $R^{31}$ and $R^{32}$ in $R^{31}O-(CH_2-O)_iR^{32}$ is H require relatively low ratios, typically, in this case, the mole ratio of formaldehyde or suitable source thereof to the carboxylic acid or ester is within the range of 1:1 to 1:9. Where neither of $R^{31}$ and $R^{32}$ is H, as for instance in $CH_3O-CH_2-OCH_3$, or in trioxane higher ratios are most preferred, typically, 6:1 to 1:3.

As mentioned above, due to the source of formaldehyde, water may also be present in the reaction mixture. Depending on the source of formaldehyde, it may be necessary to remove some or all of the water therefrom prior to catalysis. Maintaining lower levels of water than that in the source of formaldehyde may be advantageous to the catalytic efficiency and/or subsequent purification of the products. Water at less than 10 mole % in the reactor is preferred, more suitably, less than 5 mole %, most suitably, less than 2 mole %.

The molar ratio of alcohol to the acid or ester is typically within the range 20:1 to 1:20, preferably 10:1 to 1:10, most preferably 5:1 to 1:5, for example 1:1.5. However, the most preferred ratio will depend on the amount of water fed to the catalyst in the reactants plus the amount produced by the reaction, so that the preferred molar ratio of the alcohol to the total water in the reaction will be at least 1:1 and more preferably at least 2:1.

The reagents of the seventh or eighth aspect may be fed to the reactor independently or after prior mixing and the process of reaction may be continuous or batch. Typically, however, a continuous process is used.

Typically, the method of the seventh or eighth aspect of the present invention is carried out when reactants are in the gaseous phase.

In a still further aspect, the invention extends to the process of producing an ethylenically unsaturated carboxylic acid or ester according to any of the relevant aspects herein comprising the steps of first producing a catalyst according to any of the relevant aspects herein.

Definitions

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, typically, the alkyl groups are selected from methyl, ethyl, propyl, butyl, pentyl and hexyl, more typically, methyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, $-OR^{19}$, $-OC(O)R^{20}$, $-C(O)R^{21}$, $-C(O)OR^{22}$, $-NR^{23}R^{24}$, $-C(O)NR^{25}R^{26}$, $-SR^{29}$, $-C(O)SR^{30}$, $-C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (typically less than 4) oxygen, sulphur, silicon atoms, or by silano or dialkylsilcon groups, or mixtures thereof. Typically, the alkyl groups are unsubstituted, typically, linear and typically, saturated.

The term "alkenyl" should be understood as "alkyl" above except at least one carbon-carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl" except "$C_0$ alk" means non-substituted with an alkyl.

The term "aryl" when used herein includes five-to-ten-membered, typically five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "halo" when used herein means a chloro, bromo, iodo or fluoro group, typically, chloro or fluoro.

The term "Het", when used herein, includes four- to twelve-membered, typically four- to ten-membered ring systems, which rings contain one or more heteroatoms selected from nitrogen, oxygen, sulphur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein)—$OR^{19}$, $-OC(O)R^{20}$, $-C(O)R^{21}$, $-C(O)OR^{22}$, $-N(R^{23})R^{24}$, $-C(O)N(R^{25})R^{26}$, $-SR^{29}$, $-C(O)SR^{30}$ or $-C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

Suitable optional alcohols for use in the catalysed reaction of the seventh and eighth aspects of the present invention may be selected from: a $C_1$-$C_{30}$ alkanol, including aryl alcohols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, phenol, n-butanol and chlorocapryl alcohol, especially, methanol. Although the monoalkanols are most preferred, poly-alkanols, typically, selected from di-octa ols such as diols, triols, tetra-ols and sugars may also be utilised. Typically, such polyalkanols are selected from 1, 2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol. The amount of alcohol is not critical. Generally, amounts are used in excess of the amount of substrate to be esterified. Thus the alcohol may serve as the reaction solvent as well, although, if desired, separate or further solvents may also be used.

The term ageing is described in, for example, patent application WO 2009/003722. The general principles of ageing are described in The Chemistry of Silica: Solubility, Polymerisation, Colloid and Surface Properties and Biochemistry of Silica: by Ralph K Iler, 1979, John Wiley and Sons Inc., ISBN 0-471-02404-X, pages 358-364. If this stage is undertaken, the hydrogel is then washed again to remove any materials used in the ageing process and to bring the solution to the correct pH for addition of catalytically active metal which depends on the choice of salt for the catalytically active metal.

The term "gel" as used herein is also known to the skilled person but in case of doubt may be taken to be a solid network in which a fluid is dispersed. Generally, the gel is a polymer network in which fluid is dispersed. A co-gel is a term used to indicate that more than one original chemical compound/moiety is incorporated into the polymeric network, usually silica and a metal oxide or salt. Accordingly, co-gelation herein means the formation of a co-gel.

A gel is thus a sol that has set. A Hydrogel is thus a gel as defined herein where the fluid is water. A Xerogel is a gel that has been dried to remove the fluid. An Aerogel is a gel in which the fluid is replaced by a gas and therefore is not subject to the same shrinkage as a Xerogel.

The term commencement herein means the beginning of the formation of the modified silica.

The term "moieties" as used herein in relation to the metal is used to refer to the form of the modifier metal on the modified support. Although, the modifier metal generally forms part of a network, the modifier metal will be in the form of discrete residues on the silica substrate. The term mononuclear means having a single metal centre and in the case of moieties on the silica means having the form of a mononuclear residue.

% of the modifier metal has no units herein because it refers to number of metal atoms per total number of such atoms. It will be appreciated that the moieties may take the form of non-mononuclear clusters but that these clusters are still made up of modifier metal atoms.

The term "surface" as used herein in relation to the silica support, unless stated otherwise, includes the surface of the silica within the pores of the silica, more particularly, within the macro- and mesopores thereof.

Embodiments of the invention will now be defined by reference to the accompanying examples.

EXPERIMENTAL

Silica Support Description

Example 1 (Preparative)

Fuji Silysia CARiACT Q10 silica was dried in a laboratory oven at 160° C. for 16 hours, after which it was removed from the oven and cooled to room temperature in a sealed flask stored in a desiccator. This silica had a surface area of 333 m$^2$/g, a pore volume of 1.0 ml/g, and an average pore diameter of 10 nm as determined by nitrogen adsorption/desorption isotherm analysis (Micromeretics Tristar II). A silanol number of 0.8 OH/nm$^2$ was found through TGA analysis. This silica is primarily composed of spherical silica beads in the diameter range of 2.0-4.0 mm.

Ti Modification of Silica Supports

Example 2 (0.6 wt % Ti from Ti("OPr)$_2$(acac)$_2$) (Monomer)

0.330 g of Ti("OPr)$_4$ (98%, Sigma Aldrich) was dissolved in 11 ml of 1-PrOH (99.7% anhydrous, Sigma Aldrich). To this solution, 0.348 g of acetyl acetone (Sigma Aldrich) was added and agitation was effected for 30 min at room temperature to allow Ti-complex formation. In a separate flask 10 g of the silica from Example 1 was weighed off. The weighed off silica was then added to the Ti-complex solution with agitation. Agitation was continued until all of the Ti-complex solution had been taken up into the pore volume of the silica. Once pore filling had been completed the Ti-modified silica was left for 16 hours in a sealed flask with periodic agitation. After this time the extra-porous solution was removed by filtration. This was followed by a drying step where the intra-porous organic solvent was removed by passing a flow of nitrogen gas over the wet Ti-modified silica at room temperature. Alternatively, the intra-porous solvent was removed on a rotary evaporator at reduced pressure. Once all of the solvent had been removed the Ti-modified silica support was calcined in a furnace at 500° C. under a flow of air with a heating ramp rate of 5° C./min and a final hold of 5 hours. Upon cooling this yielded the Ti modified silica support with a 100% Ti usage efficiency. The Ti load (wt %) on the Ti-modified support was determined via powder Energy Dispersive X-Ray Fluorescence analysis (Oxford Instruments X-Supreme8000).

Example 3 (1.1 wt % Ti from Ti("OPr)$_2$(acac)$_2$) (Monomer)

A support modification as described in Example 2 was performed except that 0.665 g of Ti("OPr)$_4$, 0.703 g of acetyl acetone was used. Additionally, 16 ml of 1-PrOH was used instead of 11 ml. This resulted in the Ti-complex adsorption step being conducted as a slurry phase type adsorption and a Ti adsorption efficiency of 99%.

Example 4 (0.6 wt % Ti from Ti(TEA)($^i$OPr)) (Monomer)

A support modification as described in Example 2 was performed except that 0.741 g of Ti(TEA)($^i$OPr) (80 wt % in 2-PrOH, Sigma Aldrich), and no acetyl acetone was used. Additionally, 20 ml of 1-PrOH was used instead of 11 ml. This resulted in a Ti adsorption efficiency of 57%.

Example 5 (1.0 wt % Ti from Ti(TEA)($^i$OPr)) (Monomer)

A support modification as described in Example 4 was performed except that 1.510 g of Ti(TEA)($^i$OPr) was used. This resulted in a Ti adsorption efficiency of 45%.

Example 6 (2.0 wt % Ti from Ti(TEA)($^i$OPr) (Monomer)

A support modification as described in Example 4 was performed except that 2.382 g of Ti(TEA(iOPr) was used. Additionally, 10 ml of toluene (99.8% anhydrous, Sigma Aldrich) was used to dissolve the Ti(TEA)($^i$OPr) precursor instead of 1-PrOH. This solution was then which was added to the silica that had be pre-pore filled with 10 ml of toluene. This resulted in a Ti adsorption efficiency of 58%.

Example 7 (Comparative) (3.9 wt % Ti from Ti("OPr)$_4$) (Dimer)

A support modification as described in Example 4 was performed except that 2.613 g of Ti("OPr)$_4$ was used and 20 ml of toluene was used instead of 1-PrOH. This resulted in a Ti adsorption efficiency of 95%.

Example 8 (Comparative) (1.8 wt % Ti from Ti("OPr)$_4$ (Dimer)

A support modification as described in Example 6 was performed except that 1.039 g of Ti("OPr)$_4$ was used. This resulted in a Ti adsorption efficiency of 100%.

Cs Modification of Modified Supports

Example 9 (3.5 wt % Cs, 0.5 wt % Ti)

0.514 g of CsOH·H$_2$O (99.5% Sigma Aldrich) was weighed out in a glovebox and dissolved in 20 ml of a 9:1 v/v MeOH:H$_2$O (MeOH from Sigma Aldrich, H$_2$O as demineralised water) solvent mixture. 10 g of the modified silica from Example 2 was added to the CsOH solution with agitation. Agitation was continued for an additional 15 min after which the sample was left for 16 hours in a sealed flask with periodic agitation. After this time the extra-porous solution was removed by filtration. This was followed by a drying step where the intra-porous solvent was removed by passing a flow of nitrogen gas over the wet Cs/Ti-modified silica at room temperature. Alternatively, the intra-porous solvent was removed on a rotary evaporator at reduced pressure. Following this step the catalyst beads were placed into a drying oven at 120° C. and left to dry for 16 hours. Upon cooling this yielded the Cs/Ti/SiO$_2$ catalyst with a 90% Cs usage efficiency. The Cs load (wt %) on the catalyst was determined via powder Energy Dispersive X-Ray Fluorescence analysis (Oxford Instruments X-Supreme8000).

Example 10 (4.0 wt % Cs, 0.5 wt % Ti)

A catalyst was prepared as described in Example 9 except that 0.583 g of CsOH·H$_2$O was used.

Example 11 (4.4 wt % Cs, 0.5 wt % Ti)

A catalyst was prepared as described in Example 9 except that 0.647 g of CsOH·H$_2$O was used.

Example 12 (5.3 wt % Cs, 0.5 wt % Ti)

A catalyst was prepared as described in Example 9 except that 0.795 g of CsOH·H$_2$O was used.

Example 13 (6.6 wt % Cs, 1.0 wt % Ti)

A catalyst was prepared as described in Example 9 except that 1.01 g of CsOH·H$_2$O was used and modified silica from Example 3 was used.

Example 14 (7.7 wt % Cs, 1.0 wt % Ti)

A catalyst was prepared as described in Example 13 except that 1.17 g of CsOH·H$_2$O was used.

Example 15 (8.4 wt % Cs, 1.0 wt % Ti)

A catalyst was prepared as described in Example 13 except that 1.30 g of CsOH·H$_2$O was used.

Example 16 (9.9 wt % Cs, 1.0 wt % Ti)

A catalyst was prepared as described in Example 13 except that 1.55 g of CsOH·H$_2$O was used.

Example 17 (4.0 wt % Cs, 0.6 wt % Ti)

A catalyst was prepared as described in Example 9 except that 0.59 g of CsOH·H$_2$O was used and modified silica from Example 4 was used.

Example 18 (4.8 wt % Cs, 0.6 wt % Ti)

A catalyst was prepared as described in Example 17 except that 0.71 g of CsOH·H$_2$O was used.

Example 19 (5.2 wt % Cs. 0.6 wt % Ti)

A catalyst was prepared as described in Example 17 except that 0.78 g of CsOH·H$_2$O was used.

Example 20 (6.3 wt % Cs, 0.6 wt % Ti)

A catalyst was prepared as described in Example 17 except that 0.95 g of CsOH·H$_2$O was used.

Example 21 (6.5 wt % Cs, 1.0 wt % Ti)

A catalyst was prepared as described in Example 9 except that 0.99 g of CsOH·H$_2$O was used and modified silica from Example 5 was used.

Example 22 (7.5 wt % Cs, 0.9 wt % Ti)

A catalyst was prepared as described in Example 21 except that 1.15 g of CsOH·H$_2$O was used.

Example 23 (9.8 wt % Cs, 0.9 wt % Ti)

A catalyst was prepared as described in Example 21 except that 1.54 g of CsOH·H$_2$O was used.

Example 24 (9.3 wt % Cs, 1.8 wt % Ti)

A catalyst was prepared as described in Example 9 except that 1.46 g of CsOH·H$_2$O was used and modified silica from Example 6 was used.

Example 25 (10.5 wt %, 1.8 wt % Ti)

A catalyst was prepared as described in Example 24 except that 1.67 g of CsOH·H$_2$O was used.

Example 26 (Comparative) (12.4 wt % Cs, 3.4 wt % Ti)

A catalyst was prepared as described in Example 9 except that 2.04 g of CsOH·H$_2$O was used and modified silica from Example 7 was used.

Example 27 (Comparative) (14.0 wt % Cs, 3.4 wt % Ti)

A catalyst was prepared as described in Example 26 except that 2.35 g of CsOH·H₂O was used.

Example 28 (Comparative) (15.2 wt % Cs, 3.3 wt % Ti)

A catalyst was prepared as described in Example 26 except that 2.58 g of CsOH·H₂O was used.

Example 29 (Comparative) (18.2 wt % Cs, 3.2 wt % Ti)

A catalyst was prepared as described in Example 26 except that 3.21 g of CsOH·H₂O was used.

Example 30 (Comparative) (9.4 wt % Cs, 1.6 wt % Ti)

A catalyst was prepared as described in Example 9 except that 2.04 g of CsOH·H₂O was used and modified silica from Example 8 was used.

Example 31 (Comparative) (10.6 wt % Cs, 1.6 wt % Ti)

A catalyst was prepared as described in Example 30 except that 1.61 g of CsOH·H₂O was used.

Example 32 (Catalytic Performance Testing)

Catalysts from Example 9 to Example 31 were tested for the reaction of methyl propionate and formaldehyde in a labscale microreactor. For this, 3 g of catalyst was loaded into a fixed bed reactor with an internal tube diameter of 10 mm as either crushed and sieved (0.1-1.0 mm particle size) or whole bead (2.0-4.0 mm particle size) particles. The reactor was heated to 330° C. and preconditioning was performed by feeding a vaporised stream comprising of 70 wt % methyl propionate, 20 wt % methanol, 6 wt % water and 4 wt % formaldehyde from a vaporiser fed by a Gilson pump at 0.032 ml/min. This preconditioning was continued overnight. After preconditioning, a feed stream comprising of 75.6 wt % methyl propionate, 18.1 wt % methanol, 5.7 wt % formaldehyde and 0.6 wt % water, was pumped by a Gilson pump to a vaporiser set at 330° C. before being fed to the heated reactor set at 330° C. containing the catalyst. The reactor exit vapour was cooled and condensed with samples being collected at five different liquid feed rates (between 0.64-0.032 ml/min) so as to obtain conversions at varying vapour/catalyst contact times. The liquid feed and condensed ex-reactor liquid products were analysed by a Shimadzu 2010 Gas Chromatograph with a DB1701 column. The compositions of the samples were determined from the respective chromatograms and yields and selectivities at varying contact times determined. Activity was defined as the inverse of the contact time, in seconds, required to obtain 10% MMA+MAA yield on methyl propionate fed and was determined via an interpolation on a contact time vs. MMA+MAA yield graph. This interpolated contact time was then used to obtain the MMA+MAA selectivity at 10% MMA+MAA yield.

TABLE 1

Activity and MMA + MAA selectivity results for catalysts prepared on the Ti modified support examples tested as whole beads.

| Example | Ti nuclearity | Ti load (wt %) | Cs load (wt %) | Cs:Ti (molar ratio) | Activity at 10% MMA + MAA yield (1/s) | MMA + MAA selectivity (%) |
| --- | --- | --- | --- | --- | --- | --- |
| Example 9 | 1 | 0.5 | 3.5 | 2.4 | 0.22 | 94.7 |
| Example 10 | 1 | 0.5 | 4.0 | 2.7 | 0.29 | 95.7 |
| Example 11 | 1 | 0.5 | 4.4 | 3.0 | 0.35 | 95.6 |
| Example 12 | 1 | 0.5 | 5.3 | 3.7 | 0.35 | 96.3 |
| Example 13 | 1 | 1.0 | 6.6 | 2.4 | 0.46 | 94.2 |
| Example 14 | 1 | 1.0 | 7.7 | 2.7 | 0.55 | 95.4 |
| Example 15 | 1 | 1.0 | 8.4 | 3.0 | 0.69 | 94.7 |
| Example 16 | 1 | 1.0 | 9.9 | 3.6 | 0.63 | 95.1 |
| Example 17 | 1 | 0.6 | 4.0 | 2.4 | 0.30 | 94.7 |
| Example 18 | 1 | 0.6 | 4.8 | 2.9 | 0.38 | 95.2 |
| Example 19 | 1 | 0.6 | 5.2 | 3.2 | 0.51 | 95.3 |
| Example 20 | 1 | 0.6 | 6.3 | 3.9 | 0.46 | 96.3 |
| Example 21 | 1 | 1.0 | 6.5 | 2.5 | 0.55 | 93.5 |
| Example 22 | 1 | 0.9 | 7.5 | 2.9 | 0.73 | 94.4 |
| Example 23 | 1 | 0.9 | 9.8 | 3.9 | 0.79 | 95.0 |
| Example 26 (comp) | 2 | 3.4 | 12.4 | 1.3 | 0.74 | 92.8 |
| Example 27 (comp) | 2 | 3.4 | 14.0 | 1.5 | 1.00 | 92.8 |
| Example 28 (comp) | 2 | 3.3 | 15.2 | 1.7 | 1.13 | 93.1 |
| Example 29 (comp) | 2 | 3.2 | 18.2 | 2.1 | 0.55 | 90.1 |

TABLE 2

Activity and MMA + MAA selectivity results for catalysts prepared on the Ti modified support examples tested as crushed beads.

| Example | Ti Nuclearity | Ti load (wt %) | Cs load (wt %) | Cs:Ti (molar ratio) | Activity at 10% MMA + MAA yield (1/s) | MMA + MAA selectivity (%) |
|---|---|---|---|---|---|---|
| Example 24 | 1 | 1.8 | 9.3 | 1.8 | 1.08 | 93.8 |
| Example 25 | 1 | 1.8 | 10.5 | 2.1 | 1.22 | 93.2 |
| Example 30 (comp) | 2 | 1.6 | 9.4 | 2.1 | 1.02 | 81.7 |
| Example 31 (comp) | 2 | 1.6 | 10.6 | 2.4 | 1.08 | 83.5 |

Example 33 (Accelerated Ageing Tests)

Catalyst sintering resistance was assessed in an accelerated ageing test. For this, 1 g of catalyst was loaded into a U-tube stainless steel reactor and loaded into an oven. The oven was heated to 385° C. and a stream of nitrogen (10 ml/min) was passed through a saturating vaporiser containing water that was heated to 92° C. This ensured that a feed stream with a water partial pressure of 0.75 bara was passed over the catalyst heated to 385° C. Periodically the surface area of the catalyst samples was determined ex-situ using nitrogen adsorption/desorption isotherm analysis (Micromeretics Tristar II). The measured surface area values were used to determine sintering rates constants for each catalyst and is described as $g^3 \cdot m^{-6} \cdot d^{-1}$. The higher the sintering rate constant, the lower the sintering resistance of the catalyst. This test was performed on catalysts from Example 9 to Example 12.

TABLE 3

Accelerated ageing data for the catalysts containing Ti as a modifier.

| | Surface area at time (days) | | | | | Catalyst activity (1/s) | Sintering rate constant ($g^3 \cdot m^{-6} \cdot d^{-1}$) |
|---|---|---|---|---|---|---|---|
| Example | 1 | 7 | 14 | 21 | 28 | | |
| Example 9 | 187 | 159 | 144 | 140 | 140 | 0.22 | 7.70E-09 |
| Example 10 | 171 | 151 | 124 | 130 | 127 | 0.29 | 1.09E-08 |
| Example 11 | 153 | 115 | 111 | 87 | 103 | 0.35 | 3.16E-08 |
| Example 12 | 119 | 98 | 86 | 82 | 89 | 0.35 | 3.51E-08 |

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the preferred, typical or optional invention features disclosed in this specification (including any accompanying claims, abstract or drawings), or to any novel one, or any novel combination, of the preferred, typical or optional invention steps of any method or process so disclosed.

The invention claimed is:

1. A method of producing an ethylenically unsaturated carboxylic acid or ester, comprising the steps of contacting formaldehyde or a suitable source thereof with a carboxylic acid or ester in the presence of catalyst and wherein the catalyst comprises a modified silica support, comprising a titanium modifier metal, and a catalytic metal on the modified silica support, wherein at least a proportion of the modified metal is present in the form of mononuclear titanium moieties or is derived from a mononuclear titanium cation source at the commencement of the modification.

2. The method according to claim 1, wherein the carboxylic acid or ester is of the formula $R^1$—$CH_2$—$COOR^3$, wherein $R^1$ is hydrogen or an alkyl group with 1 to 12 and $R^3$ is independently, hydrogen or an alkyl group with 1 to 12, and the formaldehyde or a suitable source of formaldehyde of formula (I) as defined below:

where R5 is methyl and R6 is H;

X is O;

m is 1;

and n is any value between 1 and 20 or any mixture of these.

3. The method according to claim 1, wherein the carboxylic acid or ester is selected from methyl propionate or propionic acid.

4. The method according to claim 1, wherein the step of contacting formaldehyde or a suitable source thereof with a carboxylic acid or ester in the presence of catalyst is also in the presence of an alcohol.

5. The method according to claim 4, wherein the alcohol is methanol.

6. The method according to claim 1, wherein the ethylenically unsaturated carboxylic acid or ester is selected from the group consisting of methyl methacrylate and methacrylic acid.

* * * * *